(12) United States Patent
Alba et al.

(10) Patent No.: US 7,919,463 B2
(45) Date of Patent: Apr. 5, 2011

(54) GROWTH-STIMULATING POLYPEPTIDES FOR USE IN FISH AND CRUSTACEANS

(75) Inventors: Jannel Acosta Alba, Ciudad de la Habana (CU); Mario Pablo Estrada Garcia, Ciudad de la Habana (CU); Yamila Carpio Gonzalez, Ciudad de la Habana (CU); Reynold Morales Fernandez, Ciudad de la Habana (CU)

(73) Assignee: Centro de Ingenieria Genetica y Biotecnologia, Ciudad de la Habana (CU)

( * ) Notice: Subject to any disclaimer, the term of this patent is extended or adjusted under 35 U.S.C. 154(b) by 44 days.

(21) Appl. No.: 11/989,088

(22) PCT Filed: Jun. 23, 2006

(86) PCT No.: PCT/CU2006/000006
§ 371 (c)(1), (2), (4) Date: Oct. 22, 2010

(87) PCT Pub. No.: WO2007/009403
PCT Pub. Date: Jan. 25, 2007

(65) Prior Publication Data
US 2010/0167998 A1    Jul. 1, 2010

(30) Foreign Application Priority Data
Jul. 21, 2005    (CU) ................................. 2005-0135

(51) Int. Cl.
*A61K 38/27* (2006.01)
*C07K 14/61* (2006.01)

(52) U.S. Cl. .......................................... 514/12; 530/399
(58) Field of Classification Search ........................ None
See application file for complete search history.

(56) References Cited

U.S. PATENT DOCUMENTS
2003/0084469 A1    5/2003    Chang et al.

FOREIGN PATENT DOCUMENTS
| EP | 0387457 | 9/1990 |
| EP | 1447181 A1 | 11/2004 |
| WO | WO9426897 A | 11/1994 |

OTHER PUBLICATIONS

Rentier-Delrue et al. DNA 8: 271-278, 1989.*
Ber et al. Gene 113: 245-250, 1992.*
Clara Pena et al., "Synthesis and Properties of Human Growth Hormone Fragments," Int. J. Peptide Protein Res. 18, 1981, 289-296.
Elio F. De Palo et al., "Growth Hormone Isoforms and Segments/Fragments: Molecular structure and laboratory measurement," Clinica Chimica Acta 364, 2006, 67-76.
International Search Report from PCT/CU2006/000006.
Matsuda, K. et al., "Anorexigenic action of pituitary adenylate cyclase-activating polypeptide (PACAP) in the goldfish: feeding-induced changes in the expression of mRNAs for PACAP and its receptors in the brain, and locomotor response to central injection," Neurosci. Lett., vol. 386, Sep. 2005, pp. 9-13.

* cited by examiner

*Primary Examiner* — Christine J Saoud
(74) *Attorney, Agent, or Firm* — Hoffmann & Baron, LLP (57) ABSTRACT

The present invention is related to polypeptides derived from tilapia growth hormone.

6 Claims, 3 Drawing Sheets

GROWTH-STIMULATING POLYPEPTIDES FOR USE IN FISH AND CRUSTACEANS

TECHNICAL FIELD

The present invention is related with the field of aquatic biotechnology, in particular with polypeptides with a higher activity compared to tilapia growth hormone and the use of these polypeptides to increase the survival and quality of treated larvae by immersion or as a feed additive.

PREVIOUS ART

The searches of agents that promote growth in aquatic organisms have been a focus of attention for several research laboratories. Growth hormone (GH) has been the main subject of this research.

It have been reported the presence of GH in mammals, birds, reptiles, amphibians and fish. GH or somatotropin is a polypeptide synthesized and secreted by the somatotrophos of the anterior pituitary in response to hypothalamic peptides (Barinaga M., et al. (1985) Independent effects of growth hormone releasing factor on growth hormone release and gene transcription. *Nature* 314: 279-281).

GH is involved in growth regulation, development, metabolism, appetite and osmoregulation in fish (Donaldson E. M., et al. (1979) Hormonal enhancement of growth. *Fish Physiol,* 8: 455-597). Besides its anabolic effects over the somatic post-natal growth, in fish it has also effect over the immune system cells. GH promotes T-cell proliferation. It is well documented its antigen receptor activity and its role as co-stimulator in the maturation of lymphocytes (Harris H. and Bird D. J. (1997) The effects of α-MSH and MCH on the proliferations of rainbow trout (*Oncorhynchus mykiss*) lymphocytes in vitro. In: Kawashima, S., Kikuyama, S., (Eds), *Advances in Comparative Endocrinology. Monduzzi Editoire, Bologn* pp. 1023-1026a). It is very interesting its structural similarity with a number of cytoquines such as: I L-2, I L-4, I L-5, the granulocyte colony stimulating factor, the macrophagegranulocyte stimulating factor and interferon (Sprang S. R. and Bazan J. F. (1993) Cytokine structural taxonomy and mechanisms of receptor engagement. *Curro Opin. Struc. Biol.* 3: 815-827).

In mammals, GH stimulates phagocytosis, the maturation and differentiation of thymocytes (Ortega E., et al. (1996) Effects of prolactin on the in vitro phagocytic capacity of macrophages. *Comp. Immunol. Immunopathol.* 61: 389-393) and apoptosis of T-cells producing cells (Murphy W. J. and Longo D. L. (2000) Growth hormone as an immunodulating therapeutic agent. *Immunol. Today* 121: 211-213). Similarly, it has been study the effect of GH as a lymphopoiesis and phagocytosis stimulator in *Sparus aurata* and *Sparus sarba* together with the mitogenesis of the leucocytes in *O. keta* (Sakai M., et al. (1996) Increase in Haemolytic activity of serum from rainbow trout *Oncorhyncus mykiss* injected with exogenous growth hormone. *Fish Shellfish Immunol.* 6: 615-617), phagocytosis, activation of NK cells, antibody production, the complement haemolytic activity in *Oncorhynchus mykiss* (Yada T., et al. (1999) Effects of prolactin and growth hormone on plasma immunoglobulin M levels of hipophysectomized rainbow trout, *Oncorhyncus mykiss*. *Gen. Comp. Endocrinol.* 115: 46-52) and the leukocyte respiratory burst in rainbow trout (*Oncorhynchus mykiss*) and *Dicentrarchus labrax* (Munoz P., et al. (1998) Modulation of the respiratory burst activity of Mediterranean sea bass (*Dicentrarchus labrax* L.) phagocytes by growth hormone and parasitic status. *Fish Shellfish Immunol.* 8: 25-36).

It has been demonstrated the increase in plasma GH levels as a result of transfer *Salmo trutta* from freshwater to seawater accompanied with reduced levels of thyroids hormones in correlation with an increase in phagocytic activity of the head kidney leukocytes and an increase in plasmatic lysozyme concentration. Some studies pointed out the expression of specific GH receptors and IGF receptors in lymphocytes (Tapson V. F., et al. (1988) Structural and functional characterization of the human T lymphocyte receptor for insulin-like growth factor I in vitro. *Clin, C. Invest.* 82: 950-957). It has been demonstrated the in vitro effect of IGF-I in T-cell proliferation. It is well known the inductive effect of IGF-I over Bcells, immunoglobulin and plasmatic cells. The B-cells show the highest level of expression of GH receptor (Badolato R., et al. (1994) Differential expression of surface membrane growth hormone receptor on human peripheral blood lymphocytes detected by dual fluorochrome flow cytometry. *J Clin Endocrinol Metab.* 79: 984-990).

GH can affect lymphocytes B and T indirectly through its activating effect over macrophages and monocytes (Edwards C. K., et al. (1988) A newly defined property of somatotropin: priming of macrophages for production of superoxide anion. *Science* 239: 769-771). In the last one also promote quimiotaxis. These cells also act over the lymphocytes by cytoquines secretion. GH revert NK cells deficiency (Davila D. R., et al. (1987) Role of growth hormone in regulating Tdependent immune events in aged, nude, and transgenic rodents. *Neurosci. Res.* 18: 108-116).

The DNA complementary of several fish growth hormones have been cloned and sequenced. It has been demonstrated the potent effect of recombinant GH over growth in fish by injection (Tsai H. J., et al. (1993) Expression of rainbow trout growth hormone cDNA in yeast. *Bull. Inst. Zool. Acad. Sin.* 32: 162-170) or by immersion (Moriyama S. and Kawauchi H. (1990) Growth stimulation of juvenile salmonids by immersion in recombinant salmon growth hormone. *Nippon Suisan Gakkaishi* 56: 31-34).

Human GH exists as a heterogeneous group of proteins structurally related that can be found in the pituitary gland (Baumann G., et al. (1983) The molecular nature of circulating growth hormone in normal and acromegalic man: evidence for a principal and minor monomeric forms. *J. Clin. Endocrinol. Metab.* 56: 946-952), plasma (Baumann G., et al. (1985) Molecular forms of circulating growth hormone during spontaneous secretory episodes and in the basal state. *J. Clin. Endocrinol. Metab.* 60: 1216-1220) and urine (Baumann G. and Abramson E. C. (1983) Urinary growth hormone in man: evidence for multiple molecular forms. *Endocrinology* 56: 305-311). The predominant variant of human GH is a polypeptide of 22 kDa composes by a unique polypeptide chain. This polypeptide constitute the 85% of the immunoreactives human GHs (Lewis U. J., et al. (1994) Variant forms and fragments of human growth hormone in serum. *Acta Paediatr. Suppl.* 399: 29-31). Other variants of human GH comprise a polypeptide with a single polypeptide chain with a molecular weight of 20 kDa (Lewis U. J., et al. (1978) A naturally occurring structural variant of human growth hormone. *J. Biol. Chem.* 253: 2679-2687), acetylated and deamidated 22 KDa forms (Lewis U. J., et al. (1981) Altered proteolytic cleavage of human growth hormone as a result of deamidation. *J. Biol. Chem.* 256: 11645-11650) and a truncated variant that resulted from proteolytic cleavage which has two polypeptide chains connected by a disulfure bond (Singh R. N., et al. (1974) Modified forms of human growth hormone with increased biological activities. *Endocrinology* 94: 883-891). Several studies demonstrated that the last variant is the most active. This molecule is the result of proteinases digestions between aminoacids 134 and 150 of the 22 kDa hGH (Wroblewski V. J., et al. (1991) Proteolytic cleavage of human growth hormone (hGH) by rat tissues in vitro: influence on the kinetics of exogenously administered hGH. *Endocrinology* 129: 465-474). It has been suggested that the increased biological activity of this truncated variant it is due to its increased stability and the fact that it has a lower metabolic clearance rate than the others (Baumann G. (1979) Metabolic clearance rates of isohormones of human growth hormone in man. J. *Glin. Endocrinol. Metab.* 49: 495-499).

The development of recombinant DNA technology allow us the use of bacteria and yeast as host systems for the production of proteins of interest in a relative cheap process. The yeast *Pichia pastoris* is widely use as a host to produce heterologous proteins. This organism offer the benefits of other systems such as *E. coli* related to the high levels of expression, easy handling and culture and is capable to combine these with the advantages of an eukaryotic system that realize the post-translation modifications such as proteolytic processing, refolding, glycosylation and disulfure bond formation (Higgins D. R. and Cregg J. M. (1998)

Introduction to *Pichia pastoris*. *Pichia* protocols. Humana Press Inc., Towota 1-15). As expression system, this system requires a simple genetic and molecular manipulation; it's less expensive than the expression in insect cells or mammal tissue cultures, because the mediums for growth and expression do not require special supplements. This yeast easily adapts to large scale fermentations and it has preference for the respiratory growth, a physiological characteristic which facilitate its culture at high densities.

It has been published several studies of growth stimulation using recombinant yeast expressing growth hormone. It has been demonstrated the effect over chicken growth after administration of feed enriched with recombinant *Pichia pastoris* expressing GH (Chen C. M. et al. (2000) Growth enhancement of fowls by dietary administration of recombinant yeast cultures containing enriched growth hormone. *Life Sciences* 67: 2103-2115). Besides, Tsai et al., 1993 obtained an accelerated growth by dietary administration of recombinant *Saccharomyces cerevisiae* expressing GH (Tsai H. J., et al. (1993) Enhancement of tilapia growth by dietary administration of recombinant yeast lysates as a supplement. J. *Fish. Soc. Taiwan* 20: 339-345).

It has been protected in the U.S. Pat. No. 6,239,100 a polypeptide with an activity similar to fish growth hormone and its use to promote growth and reduce larval mortality in fish.

Accelerate growth, increase survival and improve larvae quality is still one of the main problems in Aquaculture.

SUMMARY OF THE INVENTION

The present invention give a solution for the problem mentioned above with polypeptides with aminoacids sequences SEQ ID NO: 7 y 8 which show a higher activity compared with tilapia GH and its application in fish and crustaceans. As the main result, we found that these polypeptides expressed extracellular in *Pichia pastoris*, which comprise the aminoacid sequences previously described, produce an increase in growth rate, survival and larvae quality when they are administered by immersion baths or as a feed additive to fish and crustaceans. Also, they improve the immune status. It was demonstrated the superiority of the polypeptides compared with tilapia growth hormone.

The use of these polypeptides in aquaculture has several advantages: 1) they are molecules smaller than fish GH, then it can be absorbed by the organism and to reach the blood stream easily; 2) As they are fragments of fish GH, they do not have biological activity in humans; 3) they have an stronger effect over growth than fish GH; 4) They have noticeable effects over growth, survival and larvae quality in a wide range of fish species.

The U.S. Pat. No. 6,239,100 protects the use of a polypeptide with a similar activity respect to fish GH to stimulate growth and reduce the mortality of fish larvae. The sequence reported for this polypeptide has a 73% of homology compared with tilapia GH and lacks 51 nucleotides of the N-terminal. The polypeptides of our invention were obtained from tilapia growth hormone. The polypeptide SEQ ID NO: 7 lack a fragment of 46 aminoacids corresponding to the C-terminal. The polypeptide SEQ ID NO: 8 lack the same fragment at the C-terminal and 17 aminoacids at the N-terminal.

Different to the polypeptide presented in the U.S. Pat. No. 6,239,100 which have an activity similar to GH, the polypeptides of our invention have a higher activity compared to GH. This activity is not specie-specific. Besides, the polypeptide SEQ ID NO: 7 which lacks a fragment at the C-terminal has a growth promoting activity superior to the polypeptide SEQ ID NO: 8.

In the materialization of the invention, the composition which comprises any of the defined polypeptides in the aminoacids sequences SEQ ID NOS: 7 and 8 stimulate growth in fish and crustaceans.

The present invention involved the cloning of the coding sequence of the polypeptides mentioned above into a *Pichia pastoris* expression vector pPS 10.

The coding sequence for these polypeptides was obtained by Polymerase Chain Reaction (PCR) using the cDNA of tiGH previously cloned in pR 17 as template (Guillen I. I., et al. (1998) Physiological changes in the juvenile euryhaline teleost, the tilapia *Oreochromis hornorum*, injected with *E. coli*-derived homologous growth hormone. *J Mar. Biotechnol.* 6: 142-51). Tilapia growth hormone was also amplified by PCR from the same vector (pR 17).

The vector used in the genetic construction for the target proteins expression in *Pichia pastoris* contains the *Pichia pastoris* AOX1 promoter (pAOX1), the signal peptide of *S. cerevisiae* sucrose invertase 2 (spSUC 2) and the termination signal of the enzyme glyceraldehide-3P-deshydrogenase (GAPt) of *S. cerevisiae*. It contains also a fragment of chromosomal DNA corresponding to the 3' AOX region necessary for the homologous recombination between the yeast and HIS3 gene of *S. cerevisiae* which is the yeast selection marker. The vector has a functional replication origin in *E. coli* and the ampicillin resistance gene as a bacteria selection marker. The vectors used to generate recombinant *Pichia pastoris* strains are generally integrative. Prior to transformation the plasmids should be linearized to facilitate the homologous recombination by AOX1 gene. The *Pichia pastoris* MP36 strain was used for the extracellular production of the recombinant proteins. This strain is a his3 auxotrophic mutant obtained from *Pichia pastoris* BKM-90 strain (EP 00438200) that acquired the phenotype His+ after transformation with the expression vector (Yong V., et al. (1992) HIS-3 gene of *Saccharomyces cerevisiae* complement his mutation in yeast *Pichia pastoris*. *Biotecnologia Aplicada* 9: 55-61).

Several studies have been demonstrated a growth stimulating effect by administration via immersion of recombinant GH in different fish species. Nevertheless, this invention is the first report of growth stimulation in fish by immersion into *Pichia pastoris* culture supernatants containing polypeptides with a higher activity compared to GH without previous purification of the target proteins.

The effect of the polypeptides described in the present invention, over growth, pathogen resistant and immune system parameters, was tested in tilapia larvae and compared with tilapia growth hormone.

The treatments were administered via immersion. The experimental groups were:
- Culture supernatants of recombinant *Pichia pastoris* MP36 strain which contain the polypeptides
- Culture supernatants of recombinant *Pichia pastoris* MP36 strain which contain the tilapia GH.
- A negative control contain culture supernatants of non-transformed *Pichia pastoris* M P36
- Non-treated group.

The results showed that the group treated with the polypeptides significantly increase its weight compared with tiGH, negative control and non-treated groups. To analyze the effect over the immune system, 20 animals were homogenized.

The presence of different non-specific humoral factors such as lysozyme and lectins and the following parameters of oxidative stress were measured.
- Reduced glutathione: GSH is a cofactor of the enzyme glutathione peroxidase. It is one of the defense mechanisms against oxidative stress. We didn't find any statistical difference between groups. Nevertheless, there is a tendency to increase in the groups treated with polypeptides 1 and 2.
- Superoxide dismutase: SOD is an enzyme that belongs to the antioxidant defenses. It captures superoxide free radicals. We didn't find any statistical difference between groups. There is a tendency to increase in the groups treated with polypeptides 1 and 2.
- Total organoperoxides: It is one of the elements of the pro-oxidant system and one of the hydroxyl radical precursors. It could be also an inductor of gene expression, activation of cellular mechanism and regulator of phosphatases and kinases. It is also a cofactor for Glutathione-S-transferase which is involved in the detoxification of xenobiotics. There are not statistical significant differences between groups.
- Catalase: It is an indicator of oxidative stress that produces biomolecules oxidation. When the levels of catalase are increased indicate the presence of free radicals that can not be metabolized via glutathione peroxidase. At 21 days from the beginning of the experiment there were not statistical differences between groups. At 45 days, the catalase levels declined in the groups treated with the polypeptides respect to controls.
- Peroxidation potential. It is an indicative of lipid oxidation. We obtained statistical significant differences in treated groups compared to non-treated, with a major tendency in the groups treated with polypeptides 1 and 2.
- Protein oxidation. It is an indicative of protein oxidation. We didn't find statistical differences between groups.

Since peroxidation potential is an indicative of oxidative stress in the organisms, we can deduce that the assayed polypeptides produced some oxidative stress compared to non-treated group. The oxidative stress is an important regulatory event. At 45 days from the beginning of the experiment, even when there are oxidative stress with an effect over lipid oxidation, significantly decay the levels of catalase between treated-groups compared with non-treated. This event indicates decreased levels of free radicals and oxidative stress.

The lipids give the major ratio energy/mass compared to other biomolecules that storage energy. It has been demonstrated that GH inhibits lipogenesis and activates lipolysis and the produced fatty acids are ideal oxidative substrates. As a consequence, the aminoacids move from oxidative process to growth. The lipid oxidation observed in our experiment could be related with this process.

Other parameters related with the immune system are lysozyme and lectins. Lysozyme is one of the components of the non-specific immune functions against viral and bacterial infections. It has been observed a correlation between lysozyme levels and GH in fish (Yada T., et al. (2002) Immunomodulatory effects of prolactin and growth hormone in the tilapia, *Oreochromis mossambicus. J Endocrinol.* 173: 483-492).

Lectins react with a diverse array of pathogens and confer innate immunity to the organisms (Alexander J. B. and Ingram G. A., (1992) Noncellular nonspecific defense mechanism of fish. *Annu. Rev. Fish. Dis.* 2: 249-279).

We observed statistical significant differences in both parameters in polypeptides 1 and 2 treated-groups compared to non-treated group.

The effect of these polypeptides was also tested in ornamental fish larvae. They were capable of stimulate growth and survival in polypeptides-treated groups compared to controls. They also improve the fish pigmentation. This parameter is crucial for ornamental fish commercialization. It was demonstrated that the effect produced by these polypeptides was visible 15 days after the treatments were stopped.

DETAILED DESCRIPTION OF PARTICULAR EMBODIMENTS

Examples

Example 1

Construction of the *Pichia pastoris* Expression Vectors Containing the Coding Sequences for the Polypeptides which are the Subjects of the Present Invention and Tilapia Growth Hormone, Transformation into the MP36 Strain and Expression of the Proteins of Interest The coding sequences for the polypeptides mentioned above were obtained by PCR with specific oligonucleotides using tilapia cDNA as a template previously cloned into pR17 vector. To amplify the coding sequence for the polypeptide SEQ ID NO: 7, we used oligonucleotides corresponding to the sequences SEQ ID NO: 1 and SEQ ID NO: 2. To amplify the coding sequence for the polypeptide SEQ ID NO: 8, we used oligonucleotides corresponding to the sequences SEQ ID NO: 3 and SEQ ID NO: 4.

Figure 1:
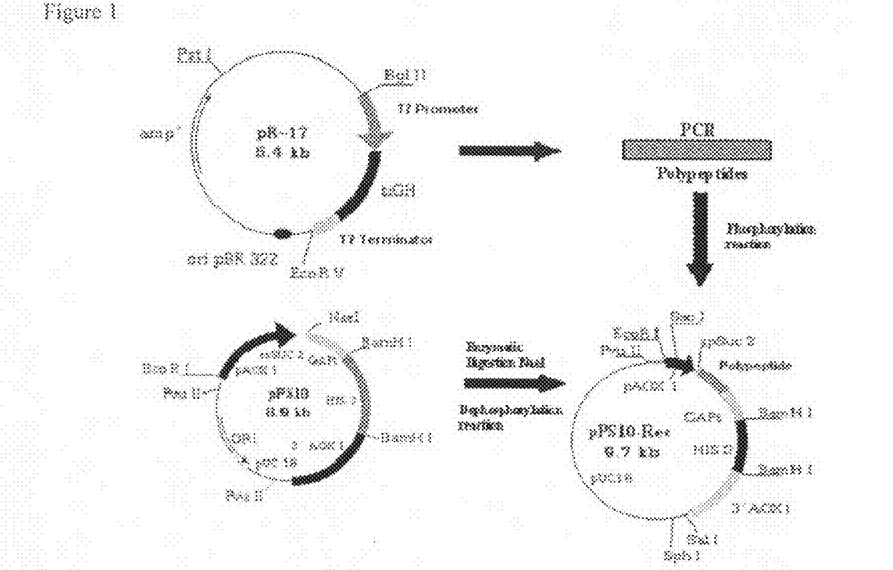
FIG. 1. Cloning strategy in the *Pichia pastoris* expression vector.

The coding sequence for tiGH was amplified by PCR from the vector pR17 using the oligonucleotides corresponding to the sequences SEQ ID NO: 5 and SEQ ID NO: 6. The PCR products were treated with the polynucleotide kinase enzyme to phosphorylate the ends of the gene and facilitate its cloning into an expression vector. The *Pichia pastoris* expression vector pPS 10 was enzymatic digested with the restriction endonuclease Nae I and treated with alkaline phosphatase to dephosphorylate the ends. The genes encoding for the interested polypeptides and tiGH were ligated into the expression vector using T4 DNA ligase (FIG. 1). Prior to transformation, the plasmids were linearized with the enzyme Sph I. The *Pichia pastoris* MP36 strain was transformed by electroporation with the recombinant expression vector. This strain is an auxotrophic mutant his3 which acquired a His+ phenotype after transformation.

The transformants, identified by Dot Blot, were also analyzed by Southern blot to determinate in which ones the integration occurred by the replacement of the gene AOX1 of *P. pastoris* for the expression cassette of the recombinant plasmid. This integration event produces a Mut$^s$ (low levels of methanol utilization) and His+phenotypes. The genetic replacement of AOX1 occurs by recombination between the promoter regions AOX1 and 3'AOX1 in the vector and genome. As a result of the recombination, a deletion occurs in the coding region for AOX1. The recombinant strains with a Mut$^s$ phenotype support the alcohol oxidase production in the AOX2 gene and they have a low growth rate in methanol.

Figure 2:
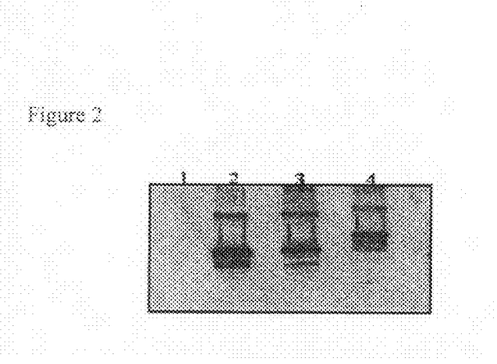
FIG. 2. Expression analysis of transformants which show a Mut$^s$ phenotype. Western blot of the target proteins expressed in *Pichia pastoris* culture supernatants. Line 1: Non-transformed MP36; Line 2: Polypeptide 1; Line 3: Polypeptide 2; Line 4: tilapia growth hormone.

The genes encoding for the interested polypeptides and tilapia growth hormone are under the regulation of the AOX1 promoter, inducible by methanol, and they have a signal peptide. *Pichia pastoris* secrete low levels of self proteins and its culture medium does not need proteins as supplements. Therefore, it can be expected that a secreted heterologous protein will be a high percent of the total proteins in the medium (more than 80%) (Tschopp y col.; Bio/Technology 1987, 5: 1305-1308; Barr et al.; Pharm. Eng. 1992, 12: 48-51). The production of the recombinant proteins explained in this invention was done in bioreactors of 5 L with the addition of methanol to the culture. As it's shown in FIG. 2, a Western blot using a monoclonal antibody specific for tilapia GH was used to check the expression of the protein in culture supernatants.

Example 2

Growth Experiment in Tilapia by Immersion with *P. pastoris* Culture Supernatants Containing Polypeptides of Interest. Effect Over the Immune System The experiment was done by immersion, three times a week for 90 min. The dose was 0.1 mg of target protein/liter of water. The experimental groups were:
1. Group treated with the *P. pastoris* culture supernatant containing polypeptide 1 (treatment 1).
2. Group treated with the *P. pastoris* culture supernatant containing polypeptide 2 (treatment 2).
3. Group treated with the *P. pastoris* culture supernatant containing tilapia GH (treatment 3)
4. Negative control group treated with non-transformed *P. pastoris* culture supernatant (negative control).
5. Non-treated group.

Figure 3:
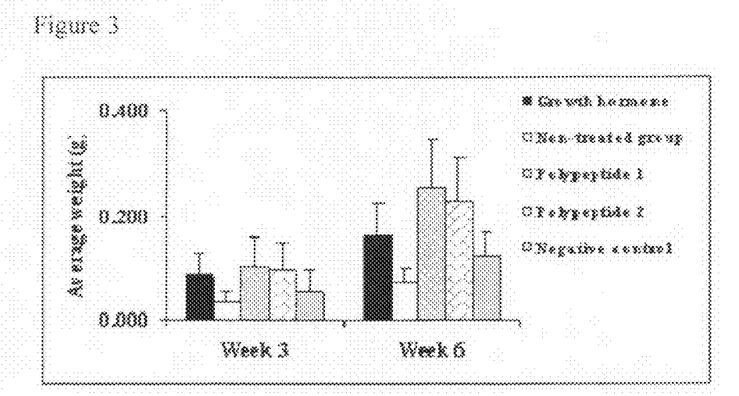
FIG. 3. Growth experiment in tilapia larvae by immersion in *Pichia pastoris* culture supernatants containing the proteins of interest at the dose of 0.1 mg/liter of water. Graphic represents the average body weight of treated-groups compared to negative controls.

At 45 days from the beginning of the experiment larvae treated with the polypeptide SEQ ID NO: 7 had a weight increase 3.6, 2.1 and 1.6 fold higher compared with non-treated group, negative control and tiGH treated group, respectively. On the other hand, larvae treated with the polypeptide SEQ ID NO: 8 had a weight increase 3.2 fold higher compared with non-treated group, 1.9 fold compared with negative control and 1.4 fold compared to tiGH treated group (Table 1, Table 1.1, FIG. 3).

TABLE 1

| | Average in the body weight of groups (g). | | | | |
|---|---|---|---|---|---|
| | Negative control | Growth hormone | Non-treated group | Polypeptide SEQ ID No. 7 | Polypeptide SEQ ID No. 8 |
| Week 3 | 0.055 ± 0.037 | 0.084 ± 0.042 | 0.033 ± 0.020 | 0.099 ± 0.058 | 0.092 ± 0.055 |
| Week 6 | 0.120 ± 0.046 | 0.159 ± 0.067 | 0.071 ± 0.026 | 0.254 ± 0.093 | 0.227 ± 0.082 |

Mass is shown as mean ± S.D

TABLE 1.1

Statistical analysis at 45 days from the beginning of the experiment.

| Tukey's Multiple Comparison Test | P value |
|---|---|
| Negative control vs Growth hormone | P > 0.05 |
| Negative control vs Polypeptide SEQ ID No. 8 | P < 0.001 |
| Negative control vs Polypeptide SEQ ID No. 7 | P < 0.001 |
| Negative control vs Non-treated group | P < 0.05 |
| Growth hormone vs Polypeptide SEQ ID No. 8 | P < 0.01 |
| Growth hormone vs Polypeptide SEQ ID No. 7 | P < 0.001 |
| Growth hormone vs Non-treated group | P < 0.001 |
| Polypeptide SEQ ID No. 8 vs Polypeptide SEQ ID No. 7 | P > 0.05 |
| Polypeptide SEQ ID No. 8 vs Non-treated group | P < 0.001 |
| Polypeptide SEQ ID No. 7 vs Non-treated group | P < 0.001 |

These are very important results since the growth acceleration at early developmental stages of economical important fishes produce a survival increase that is crucial to increase cultures productivities.

To analyze the effect over the immune system, 20 animals per group were taken at 21 and 45 days from the beginning of the experiment. The larvae were homogenized and different parameters of the oxidative stress were measure:

GSH, SOD, total organoperoxides, catalase, peroxidation potential and protein oxidation.

We only observed differences in peroxidation potential between treated groups compared with negative control at 21 days from the beginning of the experiment.

We measured lysozyme activity in larvae extracts of 45 days from the beginning of the experiment. The lysozyme activity of samples (larval homogenates) was measured using a method based on the ability of lysozyme to lyse the bacterium *Micrococcus lysodeikticus*. In a 96-well microtray, 100 µL of samples in four twofold serial dilutions in phosphate buffer (0.05 M, pH 6.2) were mixed with 100 µL of a 3 mg/ml suspension of *Micrococcus lysodeikticus* (Sigma). The microtray was incubated at 22° C. and the O.D. was read at 450 nm at 0, 15, 30 and 60 min. For a positive control, larval homogenates was replaced by hen egg white lysozyme (serial dilutions starting at 8 µg/mL) and for a negative control, buffer replaced larval homogenates. A unit of lysozyme activity was defined as the amount of larval homogenates causing a decrease in the O.D. reading of 0.001 $min^{-1}$. We observed statistical significant differences between treated groups with the polypeptides SEQ ID NO: 7 and SEQ ID NO: 8 compared with non-treated group (Table 2).

We made also a haemagglutination assay to measure lectins in larval homogenates. Serial twofold dilutions of larvae extracts were performed using PBS pH 7.2 in U-bottom shaped (96 wells, Greiner, Microlon) microtitre wells to which an equal volume of freshly prepared 2% erythrocyte suspension (rabbit in PBS) was added. Wells were incubated for 1 h at room temperature and the titer was read visually and being equal to the dilution in the last well to show agglutination (as manifested by an evenly distributed layer of cells over the whole well bottom). The haemagglutinin activity of samples was examined and for each titer value was obtained. The activity was expressed as titre, i.e. the reciprocal of the highest dilution showing complete agglutination.

We observed statistical significant differences between treated groups with the polypeptides SEQ ID NO: 7 and SEQ ID NO: 8 compared with non-treated group (Table 3).

TABLE 3

Titer of haemagglutinin activity (the reciprocal of the highest dilution showing complete agglutination) in the larvae extracts at 45 days from beginning of the experiment.

| | Polypeptide SEQ ID No. 7 | Polypeptide SEQ ID No. 8 | Growth hormone | Negative control | Non-treated group |
|---|---|---|---|---|---|
| Titulo | 4* | 4* | 2 | 2 | 1 |

ANOVA, Turkey's test;
*indicates a significant difference P < 0.05

Example 3

Growth Stimulation Experiment and Improvement in Larvae Quality in Goldfish by Immersion Baths with *Pichia pastoris* Culture Supernatants Containing the Polypeptides of Interest Four experimental groups were designed. The treatments consisted of immersion baths, three times a week for 90 min. The dose was 0.1 mg of target protein/liter of water. The experimental groups were:

1. Group treated with the *P. pastoris* culture supernatant containing polypeptide 1 (treatment 1).
2. Group treated with the *P. pastoris* culture supernatant containing polypeptide 2 (treatment 2).
3. Group treated with the *P. pastoris* culture supernatant containing tilapia GH (treatment 3)
4. Negative control group treated with non-transformed *P. pastoris* culture supernatant (negative control).

At 45 days from the beginning of the experiment, the treatments 1 and 2 showed a significant weight increase compared with treatments 3 and 4.

Figure 4:
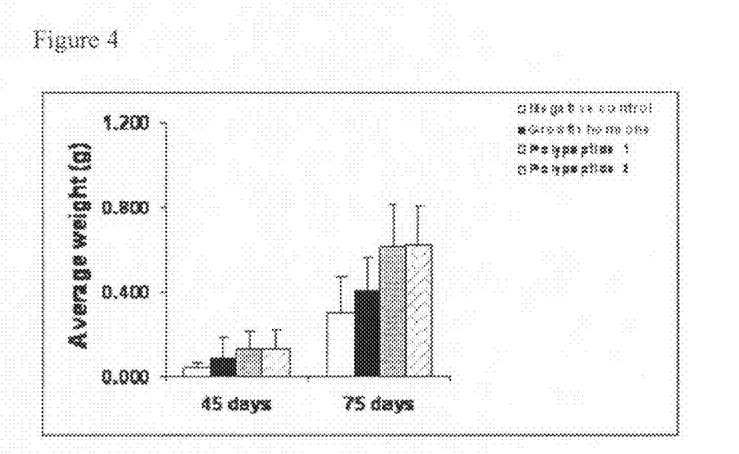
FIG. 4. Growth experiment in goldfish larvae by immersion in *Pichia pastoris* culture supernatants containing the proteins of interest at the dose of 0.1 mg/liter of water. Graphic represents the average body weight of treated-groups compared to negative controls.
Figure 5:
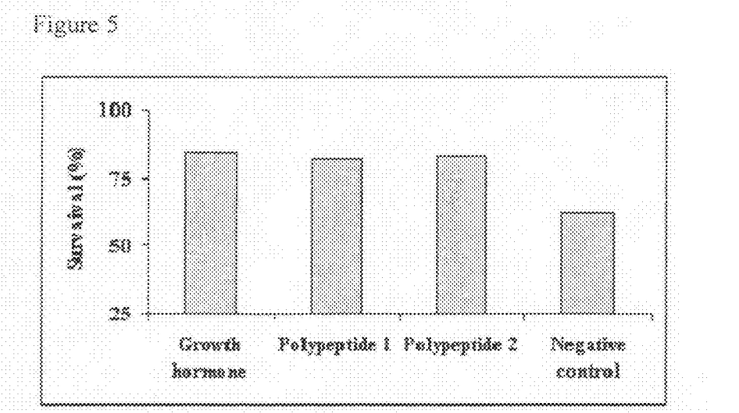
FIG. 5. Growth experiment in goldfish larvae by immersion in *Pichia pastoris* culture supernatants containing the proteins of interest at the dose of 0.1 mg/liter of water. Graphic represents the survival percent of the experimental groups 45 days from the beginning of the experiment.

At 75 days, larvae treated with polypeptides SEQ ID NO: 7 and SEQ ID NO: 8 had a weight increase 2 times higher compared with negative control and 1.5 compared with tiGH treated group (Table 4; Table 4.1; FIG. 4). Besides, the treatments 1, 2 and 3 showed an increase in survival compared with negative control (FIG. 5).

Figure 6:
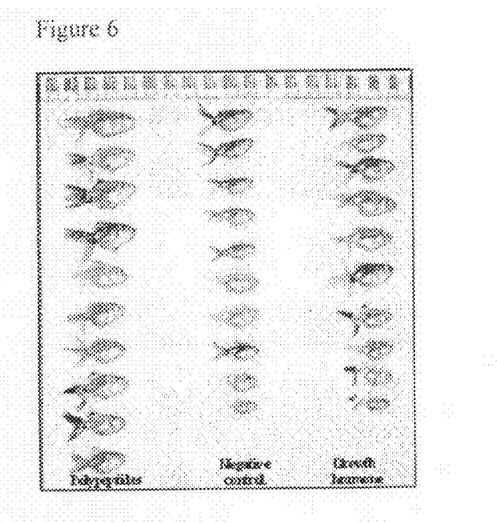
FIG. 6. Growth experiment in goldfish larvae by immersion in *Pichia pastoris* culture supernatants containing the proteins of interest—at the dose of 0.1 mg/liter of water. The treated fishes show more brilliant colours than negative controls.

The color of the ornamental fish is a very important parameter for its commercialization. In this experiment, we observed that larvae under treatments 1 and 2 showed color in an early developmental stage compared with negative control. At 75 days from the beginning of the experiment they had more brilliant colors (FIG. 6).

We obtained similar results with other ornamental fish species.

TABLE 2

Lyzozyme concentration (µg/mL) in the larvae extracts at 45 days from begining of the experiment.

| Polypeptide SEQ ID No. 7 | Polypeptide SEQ ID No. 8 | Growth hormone | Negative control | Non-treated group |
|---|---|---|---|---|
| 2.596 ± 0.425* | 2.598 ± 0.430* | 2.250 ± 0.162 | 2.246 ± 0.160 | 1.404 ± 0.700 |

The concentration is shown as means ± S.D
ANOVA, Turkey's test;
*indicates a significant difference P < 0.05

TABLE 4

Average in the body weight of groups (g).

|  | Polypeptide SEQ ID No. 7 | Polypeptide SEQ ID No. 8 | Growth hormone | Negative control |
|---|---|---|---|---|
| 45 days | 0.132 ± 0.083 | 0.137 ± 0.088 | 0.087 ± 0.099 | 0.042 ± 0.024 |
| 75 days | 0.613 ± 0.198 | 0.625 ± 0.184 | 0.405 ± 0.156 | 0.307 ± 0.169 |

Mass is shown as mean ± S.D

TABLE 4.1

Statistical analysis at 75 days from the beginning of the experiment.

| Tukey's Multiple Comparison Test | P value |
|---|---|
| Negative control vs Growth hormone | P > 0.05 |
| Negative control vs Polypeptide SEQ ID No. 8 | P < 0.001 |
| Negative control vs Polypeptide SEQ ID No. 7 | P < 0.001 |
| Growth hormone vs Polypeptide SEQ ID No. 8 | P < 0.001 |
| Growth hormone vs Polypeptide SEQ ID No. 7 | P < 0.001 |
| Polypeptide SEQ ID No. 8 vs Polypeptide SEQ ID No. 7 | P > 0.05 |

Example 4

Growth Experiment in Carps by Immersion Baths with Different Doses of Polypeptide 1

Figure 7:
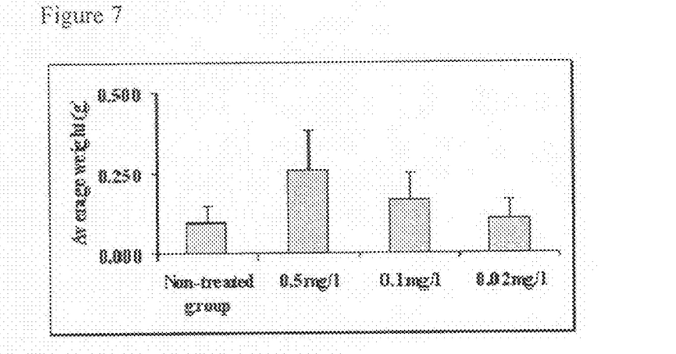
FIG. 7. Growth experiment in carp larvae by immersion in *Pichia pastoris* culture supernatants containing polypeptide 1 at three different doses (0.02; 0.1 and 0.5 mg per liter of water). Graphic represents the average body weight of treated-group compared to negative control.

We examined the effect of different doses of the polypeptide 1 over growth in carp larvae. Four experimental groups were designed:

1. Group treated with the *P. pastoris* culture supernatant containing polypeptide SEQ ID NO: 7 at the dose of 0.02 mg of polypeptide/liter of water (treatment 1).
2. Group treated with the *P. pastoris* culture supernatant containing polypeptide SEQ ID NO: 7 at the dose of 0.1 mg of polypeptide/liter of water (treatment 2).
3. Group treated with the *P. pastoris* culture supernatant containing polypeptide SEQ ID NO: 7 at the dose of 0.5 mg of polypeptide/liter of water (treatment 3).
4. Non-treated group At 30 days from the beginning of the experiment the larvae treated with the dose of 0.5 mg of polypeptide SEQ ID NO: 7/liter of water had a weight increase 2.75 fold higher compared with non-treated group. On the other hand, the larvae treated with 0.1 mg of polypeptide SEQ ID NO: 7/liter of water had a weight increase 1.8 fold higher compared with non-treated group. There were not statistical differences between non-treated group and the group treated with the minimal dose (Table 5; Table 5.1; FIG. 7).

TABLE 5

Average in the body weight of groups (g).

|  | Non-treated group | Dose 0.5 mg/L | Dose 0.1 mg/L | Dose 0.02 mg/L |
|---|---|---|---|---|
| 30 days | 0.094 ± 0.055 | 0.258 ± 0.127 | 0.169 ± 0.080 | 0.108 ± 0.059 |

Mass is shown as mean ± S.D

TABLE 5.1

Statistical analysis at 30 days from the beginning of the experiment.

| Tukey's Multiple Comparison Test | P value |
|---|---|
| 0.5 mg/l vs 0.1 mg/l | P < 0.01 |
| 0.5 mg/l vs 0.02 mg/l | P < 0.001 |
| 0.5 mg/l vs control | P < 0.001 |
| 0.1 mg/l vs 0.02 mg/l | P < 0.05 |
| 0.1 mg/l vs control | P < 0.01 |
| 0.02 mg/l vs control | P > 0.05 |

Example 5

Growth Experiment in Shrimp *Litopenaeus schmitti* Larvae by Immersion in *P. pastoris* Culture Supernatants Containing Polypeptides of Interest Three experimental groups were designed. The treatments consisted of immersion baths three times a week for 1:30 h. The dose was 0.1 mg of interested protein/liter of water. The experimental groups were:

1. Group treated with the *P. pastoris* culture supernatant containing polypeptide SEQ ID NO: 7 (treatment 1).
2. Group treated with the *P. pastoris* culture supernatant containing polypeptide SEQ ID NO: 8 (treatment 2).
3. Negative control group treated with non-transformed *P. pastoris* culture supernatant (negative control).

As the result of the experiment, we obtained an improvement in larvae quality in the shrimps treated with the interested polypeptides. Larvae treated with polypeptides SEQ ID NO: 7 and SEQ ID NO: 8 had an increase in body weight 2.3 fold higher relative to negative control, more branquial ramifications and rostral modifications. The corresponding statistical test was made for each parameter and statistical significant differences were found in all cases.

Example 6

Growth Experiment in Tilapia by Feed Administration of Polypeptide SEQ ID NO: 7 at Different Doses We measured the effect of two doses of the polypeptide SEQ ID NO: 7 over growth in juvenile tilapia with an initial weight of 72.99±3.25 g. The doses tested were 4.8 mg of the polypeptide SEQ ID NO: 7/Kg of feed and 38.4 mg of the polypeptide SEQ ID NO: 7/Kg of feed. Oral formulation was made by incorporating the *Pichia pastoris* culture supernatant containing the polypeptide of interest in the basal diet. The negative control was tilapia fed with basal diet enriched with non-transformed *P. pastoris* culture supernatant. During the experiment the animals were fed twice a day with the feed equivalent to the 5% of body weight for 6 weeks.

Figure 8:
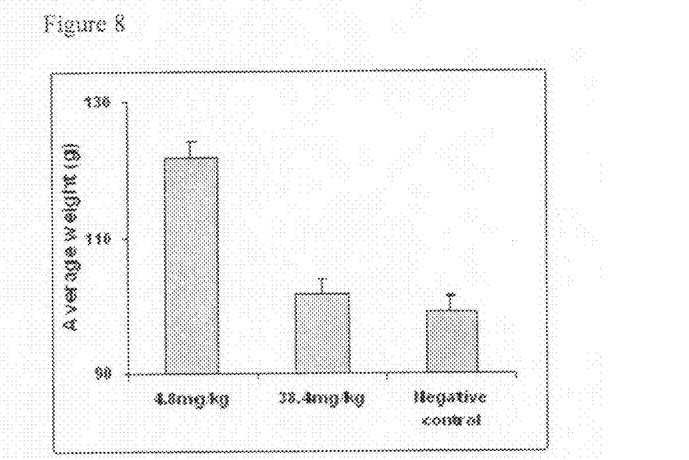
FIG. 8. Growth experiment in tilapia by feed administration of the *Pichia pastoris* culture supernatants containing polypeptide 1 at two different doses (4.8 mg of the polypeptide/Kg of feed and 38.4 mg of the polypeptide/Kg of feed). Graphic represent the average body weight of treated-groups compared to negative control.

The polypeptide SEQ ID NO: 7 included in the diet at the dose of 4.8 mg of the polypeptide SEQ ID NO: 7/Kg of feed increased growth in 22% compared with control group with highly significant statistical differences (p<0.001). The dose of 38.4 mg of the polypeptide SEQ ID NO: 7/Kg of feed didn't show differences in relation to negative control. (Table 6; Table 6.1; FIG. 8)

TABLE 6

| | Average weight of fish (g). | | |
|---|---|---|---|
| | Negative control | Dose 4.8 mg/Kg | Dose 38.4 mg/Kg |
| 45 days | 99.06 ± 2.27 | 121.82 ± 2.35 | 101.54 ± 2.39 |

Mass is shown as mean ± S.D

TABLE 6.1

| Statistical analysis at 45 days from the beginning of the experiment. | |
|---|---|
| Tukey's Multiple Comparison Test | P value |
| 4.8 mg/kg vs 38.4 mg/kg | P < 0.001 |
| 4.8 mg/kg vs control | P < 0.001 |
| 38.4 mg/kg vs control | P > 0.05 |

Nowadays, aquatic organisms are an important source of proteins, but the capture on its natural environment is fully exploited. For this reason, to increase the production it is necessary the culture of these aquatic species. It has been demonstrated that in most of the organisms exist a wide range in which it's possible to manipulate growth by hormones administration, genetic modification, etc (Pullin y col.; Conference Proceeding 7, 432 p. International Center for living Aquatic Resources Management. Manila, Philippines. 1982, ISSN 0115-4389). The polypeptides presented here have the advantage that they are not speciespecific and therefore, they are applicable for different aquatic organisms for multiple functions like increase growth, survival and larvae quality, and improve different parameters involved in the immune response. Besides, it was demonstrated that they have an effect over growth significantly higher compared with growth hormone. On the other hand, these polypeptides don't have biological activity in humans, diminishing the inconvenience that the products applicable to animals for human consumption have. Besides, the use of these polypeptides in ornamental fish is very attractive not only because they reduce the culture time as a consequence of growth acceleration, since they also have an effect over colors in this fishes.

The invention claimed is:

1. An isolated polypeptide comprising a polypeptidic chain having the sequence of amino acids identified in SEQ ID NO: 7 or SEQ ID NO: 8.

2. A method for stimulating growth in fish and crustaceans, said method comprising administering to said fish and crustaceans an isolated polypeptide comprising a polypeptidic chain having the sequence of amino acids identified in SEQ ID NO: 7 or SEQ ID NO: 8.

3. A method for stimulating growth or resistance to diseases in fish or crustaceans, said method comprising administering to said fish and crustaceans feed formulations comprising *Pichia pastoris* culture supernatants comprising polypeptides at a dose of at least 4.8 mg polypeptide per Kg of feed, said polypeptides comprising an isolated polypeptidic chain having the sequence of amino acids identified in SEQ ID NO: 7 or SEQ ID NO: 8.

4. A method according to claim 3, wherein said fish is an ornamental fish.

5. A method for stimulating growth, survival, and larvae quality for fish or crustaceans, said method comprising immersing said fish and crustaceans in water comprising *Pichia pastoris* culture supernatants comprising polypeptides present in a concentration between 0.05 and 0.5 mg of the polypeptide per liter of water, said polypeptides comprising an isolated polypeptidic chain having the sequence of amino acids identified in SEQ ID NO: 7 or SEQ ID NO: 8.

6. A method for stimulating the humoral innate immune system of fish or crustaceans, said method comprising administering to said fish or crustaceans polypeptides comprising an isolated polypeptidic chain having the sequence of amino acids identified in SEQ ID NO: 7 or SEQ ID NO: 8.

* * * * *

SEQUENCE LISTING

```
<160> NUMBER OF SEQ ID NOS: 8

<210> SEQ ID NO 1
<211> LENGTH: 22
<212> TYPE: DNA
<213> ORGANISM: Artificial Sequence
<220> FEATURE:
<223> OTHER INFORMATION: Synthetic sequence

<400> SEQUENCE: 1
atgaactcag tcgtcctcct gc                                          22

<210> SEQ ID NO 2
<211> LENGTH: 22
<212> TYPE: DNA
<213> ORGANISM: Artificial Sequence
<220> FEATURE:
<223> OTHER INFORMATION: Synthetic sequence

<400> SEQUENCE: 2
tcaatagttt ccgtaaggag cg                                          22

<210> SEQ ID NO 3
<211> LENGTH: 22
<212> TYPE: DNA
<213> ORGANISM: Artificial Sequence
<220> FEATURE:
<223> OTHER INFORMATION: Synthetic sequence

<400> SEQUENCE: 3
atgcagcaga tcacagacag cc                                          22

<210> SEQ ID NO 4
<211> LENGTH: 22
<212> TYPE: DNA
<213> ORGANISM: Artificial Sequence
<220> FEATURE:
<223> OTHER INFORMATION: Synthetic sequence

<400> SEQUENCE: 4
tcaatagttt ccgtaaggag cg                                          22
```

```
<210> SEQ ID NO 5
<211> LENGTH: 28
<212> TYPE: DNA
<213> ORGANISM: Artificial Sequence
<220> FEATURE:
<223> OTHER INFORMATION: Synthetic sequence

<400> SEQUENCE: 5
atgaactcag tcgtcctcct gctgtcgg                                              28

<210> SEQ ID NO 6
<211> LENGTH: 29
<212> TYPE: DNA
<213> ORGANISM: Artificial Sequence
<220> FEATURE:
<223> OTHER INFORMATION: Synthetic sequence

<400> SEQUENCE: 6
ccggaattcc aatgcaacac atttatttc                                             29

<210> SEQ ID NO 7
<211> LENGTH: 158
<212> TYPE: PRT
<213> ORGANISM: Oreochromis hornorum

<400> SEQUENCE: 7

Met Asn Ser Val Val Leu Leu Leu Ser Val Val Cys Leu Gly Val Ser
1               5                   10                  15

Ser Gln Gln Ile Thr Asp Ser Gln Arg Leu Phe Ser Ile Ala Val Asn
                20                  25                  30

Arg Val Thr His Leu His Leu Leu Ala Gln Arg Leu Phe Ser Asp Phe
            35                  40                  45

Glu Ser Ser Leu Gln Thr Glu Glu Gln Arg Gln Leu Asn Lys Ile Phe
        50                  55                  60

Leu Gln Asp Phe Cys Asn Pro Asp Tyr Ile Ile Ser Pro Ile Asp Lys
65                  70                  75                  80

His Glu Thr Gln Arg Ser Ser Val Leu Lys Leu Leu Ser Ile Ser Tyr
                85                  90                  95

Gly Leu Val Glu Ser Trp Glu Phe Pro Ser Arg Ser Leu Ser Gly Gly
            100                 105                 110

Ser Ser Leu Arg Asn Gln Ile Ser Pro Arg Leu Ser Glu Leu Lys Thr
        115                 120                 125

Gly Ile Leu Leu Leu Ile Arg Ala Asn Gln Asp Glu Ala Glu Asn Tyr
    130                 135                 140

Pro Asp Thr Asp Thr Leu Gln His Ala Pro Tyr Gly Asn Tyr
145                 150                 155

<210> SEQ ID NO 8
<211> LENGTH: 142
<212> TYPE: PRT
<213> ORGANISM: Oreochromis hornorum

<400> SEQUENCE: 8

Met Gln Gln Ile Thr Asp Ser Gln Arg Leu Phe Ser Ile Ala Val Asn
1               5                   10                  15

Arg Val Thr His Leu His Leu Leu Ala Gln Arg Leu Phe Ser Asp Phe
                20                  25                  30

Glu Ser Ser Leu Gln Thr Glu Glu Gln Arg Gln Leu Asn Lys Ile Phe
            35                  40                  45

Leu Gln Asp Phe Cys Asn Pro Asp Tyr Ile Ile Ser Pro Ile Asp Lys
        50                  55                  60
```

```
His Glu Thr Gln Arg Ser Ser Val Leu Lys Leu Leu Ser Ile Ser Tyr
65                  70                  75                  80

Gly Leu Val Glu Ser Trp Glu Phe Pro Ser Arg Ser Leu Ser Gly Gly
                85                  90                  95

Ser Ser Leu Arg Asn Gln Ile Ser Pro Arg Leu Ser Glu Leu Lys Thr
            100                 105                 110

Gly Ile Leu Leu Leu Ile Arg Ala Asn Gln Asp Glu Ala Glu Asn Tyr
        115                 120                 125

Pro Asp Thr Asp Thr Leu Gln His Ala Pro Tyr Gly Asn Tyr
    130                 135                 140
```